(12) United States Patent
Deransart et al.

(10) Patent No.: US 11,179,249 B2
(45) Date of Patent: Nov. 23, 2021

(54) SHOULDER PATIENT SPECIFIC INSTRUMENT

(71) Applicant: Tornier SAS, Saint Martin (FR)

(72) Inventors: Pierric Deransart, Saint Martin d'uriage (FR); Emmanuel Francois Marie Lizee, Saint Ismier (FR); Delphine Claire Michelle Henry, Saint Ismier (FR); Jean Chaoui, Locmaria-Plouzane (FR); Gilles Walch, Lyons (FR); Pascal Boileau, Nice (FR)

(73) Assignee: TORNIER SAS, Saint Martin (FR)

( * ) Notice: Subject to any disclaimer, the term of this patent is extended or adjusted under 35 U.S.C. 154(b) by 321 days.

(21) Appl. No.: 16/521,466

(22) Filed: Jul. 24, 2019

(65) Prior Publication Data
US 2019/0343658 A1 Nov. 14, 2019

Related U.S. Application Data (62) Division of application No. 15/024,747, filed as application No. PCT/IB2014/002711 on Nov. 11, 2014, now Pat. No. 10,405,993.

(60) Provisional application No. 61/903,814, filed on Nov. 13, 2013.

(51) Int. Cl.
| | |
|---|---|
| *A61B 17/58* | (2006.01) |
| *A61B 17/60* | (2006.01) |
| *A61F 2/00* | (2006.01) |
| *A61F 2/46* | (2006.01) |
| *A61B 17/17* | (2006.01) |

(Continued)

(52) U.S. Cl.
CPC ........ *A61F 2/4612* (2013.01); *A61B 17/1739* (2013.01); *A61B 17/1778* (2016.11); *A61B 2017/568* (2013.01); *A61F 2/4081* (2013.01); *A61F 2/4603* (2013.01); *A61F 2002/4677* (2013.01)

(58) Field of Classification Search
CPC combination set(s) only.
See application file for complete search history.

(56) References Cited

U.S. PATENT DOCUMENTS

| | | |
|---|---|---|
| 4,919,670 A | 4/1990 | Dale et al. |
| 5,030,219 A | 7/1991 | Matsen, III et al. |
| 5,329,846 A | 7/1994 | Bonutti |

(Continued)

FOREIGN PATENT DOCUMENTS

| | | |
|---|---|---|
| CA | 2927086 | 4/2015 |
| CA | 2927811 | 4/2015 |

(Continued)

OTHER PUBLICATIONS

US 9,451,972 B2, 09/2016, Lang et al. (withdrawn)
(Continued)

*Primary Examiner* — Sameh R Boles
(74) *Attorney, Agent, or Firm* — Duane Morris LLP (57) ABSTRACT

A patient specific glenoid guide is provided to facilitate properly aligned implantation of a glenoid prosthesis into a patient. The guide shape is designed preoperatively based on the unique configuration of the scapula of the patient. The guide orientation is chosen preoperatively based on one or more of the bone structure of the patient, the wear pattern of the patient's glenoid cavity, the anchoring means of the glenoid prosthesis, or other aspects.

23 Claims, 5 Drawing Sheets

(51) Int. Cl.
 *A61B 17/56* (2006.01)
 *A61F 2/40* (2006.01)

(56) References Cited

U.S. PATENT DOCUMENTS

| | | |
|---|---|---|
| 5,383,938 A | 1/1995 | Rohr et al. |
| 5,531,793 A | 7/1996 | Kelman et al. |
| 5,610,966 A | 3/1997 | Martell et al. |
| 5,725,586 A | 3/1998 | Sommerich |
| 5,768,134 A | 6/1998 | Swaelens et al. |
| 5,769,856 A | 6/1998 | Dong et al. |
| 5,779,710 A | 7/1998 | Matsen, III |
| 5,807,437 A | 9/1998 | Sachs et al. |
| 5,824,078 A | 10/1998 | Nelson et al. |
| 5,824,085 A | 10/1998 | Sahay et al. |
| 6,002,859 A | 12/1999 | DiGioia, III et al. |
| 6,129,764 A | 10/2000 | Servidio |
| 6,172,856 B1 | 1/2001 | Jang |
| 6,183,519 B1 | 2/2001 | Bonnin et al. |
| 6,364,910 B1 | 4/2002 | Shultz et al. |
| 6,385,475 B1 | 5/2002 | Cinquin et al. |
| 6,432,142 B1 | 8/2002 | Kamiya et al. |
| 6,459,948 B1 | 10/2002 | Ateshian et al. |
| 6,648,894 B2 | 11/2003 | Abdelgany et al. |
| 6,772,026 B2 | 8/2004 | Bradbury et al. |
| 6,797,006 B2 | 9/2004 | Hodorek |
| 6,915,150 B2 | 7/2005 | Cinquin et al. |
| 6,944,518 B2 | 9/2005 | Roose |
| 7,468,075 B2 | 12/2008 | Lang et al. |
| 7,469,474 B2 | 12/2008 | Farrar |
| 7,534,263 B2 | 5/2009 | Burdulis, Jr. et al. |
| 7,599,539 B2 | 10/2009 | Kunz et al. |
| 7,618,451 B2 | 11/2009 | Berez et al. |
| 7,634,119 B2 | 12/2009 | Tsougarakis et al. |
| 7,648,530 B2 | 1/2010 | Habermeyer et al. |
| 7,717,956 B2 | 5/2010 | Lang |
| 7,747,305 B2 | 6/2010 | Dean et al. |
| 7,796,791 B2 | 9/2010 | Tsougarakis et al. |
| 7,799,077 B2 | 9/2010 | Lang et al. |
| 7,802,503 B2 | 9/2010 | Couvillion et al. |
| 7,822,588 B2 | 10/2010 | Mueller et al. |
| 7,831,079 B2 | 11/2010 | Kunz et al. |
| 7,927,338 B2 | 4/2011 | Laffargue et al. |
| 7,981,158 B2 | 7/2011 | Fitz et al. |
| 7,983,777 B2 | 7/2011 | Melton et al. |
| 8,007,448 B2 | 8/2011 | Barrera |
| 8,014,984 B2 | 9/2011 | Iannotti et al. |
| 8,055,487 B2 | 11/2011 | James |
| 8,062,302 B2 | 11/2011 | Lang et al. |
| 8,066,708 B2 | 11/2011 | Lang et al. |
| 8,077,950 B2 | 12/2011 | Tsougarakis et al. |
| 8,083,745 B2 | 12/2011 | Lang et al. |
| 8,094,900 B2 | 1/2012 | Steines et al. |
| 8,105,330 B2 | 1/2012 | Fitz et al. |
| 8,122,582 B2 | 2/2012 | Burdulis, Jr. et al. |
| 8,234,097 B2 | 7/2012 | Steines et al. |
| 8,337,501 B2 | 12/2012 | Fitz et al. |
| 8,337,503 B2 | 12/2012 | Lian |
| 8,337,507 B2 | 12/2012 | Lang et al. |
| 8,343,218 B2 | 1/2013 | Lang et al. |
| 8,350,186 B2 | 1/2013 | Jones et al. |
| 8,366,771 B2 | 2/2013 | Burdulis, Jr. et al. |
| 8,377,073 B2 | 2/2013 | Wasielewski |
| 8,377,129 B2 | 2/2013 | Fitz et al. |
| 8,439,926 B2 | 5/2013 | Bojarski et al. |
| 8,457,930 B2 | 6/2013 | Schroeder |
| 8,460,304 B2 | 6/2013 | Fitz et al. |
| 8,475,463 B2 | 7/2013 | Lian |
| 8,480,754 B2 | 7/2013 | Bojarski et al. |
| 8,500,740 B2 | 8/2013 | Bojarski et al. |
| 8,529,568 B2 | 9/2013 | Bouadi |
| 8,529,630 B2 | 9/2013 | Bojarski et al. |
| 8,532,806 B1 | 9/2013 | Masson |
| 8,535,319 B2 | 9/2013 | Ball |
| 8,545,509 B2 | 10/2013 | Park et al. |
| 8,545,569 B2 | 10/2013 | Fitz et al. |
| 8,551,099 B2 | 10/2013 | Lang et al. |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,585,708 B2 | 11/2013 | Fitz et al. |
| 8,617,172 B2 | 12/2013 | Fitz et al. |
| 8,617,242 B2 | 12/2013 | Philipp |
| 8,623,026 B2 | 1/2014 | Wong et al. |
| 8,634,617 B2 | 1/2014 | Tsougarakis et al. |
| 8,638,998 B2 | 1/2014 | Steines et al. |
| 8,641,716 B2 | 2/2014 | Fitz et al. |
| 8,657,827 B2 | 2/2014 | Fitz et al. |
| 8,682,052 B2 | 3/2014 | Fitz et al. |
| 8,690,945 B2 | 4/2014 | Fitz et al. |
| 8,709,089 B2 | 4/2014 | Lang et al. |
| 8,731,885 B2 | 5/2014 | Iannotti et al. |
| 8,735,773 B2 | 5/2014 | Lang |
| 8,744,148 B2 | 6/2014 | Nord et al. |
| 8,768,028 B2 | 7/2014 | Lang et al. |
| 8,771,365 B2 | 7/2014 | Bojarski et al. |
| 8,774,900 B2 | 7/2014 | Buly et al. |
| 8,775,133 B2 | 7/2014 | Schroeder |
| 8,814,942 B2 | 8/2014 | Anthony et al. |
| 8,843,229 B2 | 9/2014 | Vanasse et al. |
| 8,864,769 B2 | 10/2014 | Stone et al. |
| 8,882,847 B2 | 11/2014 | Burdulis, Jr. et al. |
| 8,884,618 B2 | 11/2014 | Mahfouz |
| 8,888,855 B2 | 11/2014 | Roche et al. |
| 8,898,043 B2 | 11/2014 | Ashby et al. |
| 8,906,107 B2 | 12/2014 | Bojarski et al. |
| 8,926,706 B2 | 1/2015 | Bojarski et al. |
| 8,932,361 B2 | 1/2015 | Tornier et al. |
| 8,932,363 B2 | 1/2015 | Tsougarakis et al. |
| 8,934,961 B2 | 1/2015 | Lakin et al. |
| 8,945,230 B2 | 2/2015 | Lang et al. |
| 8,951,259 B2 | 2/2015 | Fitz et al. |
| 8,951,260 B2 | 2/2015 | Lang et al. |
| 8,965,088 B2 | 2/2015 | Tsougarakis et al. |
| 8,971,606 B2 | 3/2015 | Chaoui |
| 8,974,539 B2 | 3/2015 | Bojarski et al. |
| 8,984,731 B2 | 3/2015 | Broeck et al. |
| 8,989,460 B2 | 3/2015 | Mahfouz |
| 8,992,538 B2 | 3/2015 | Keefer |
| 8,998,915 B2 | 4/2015 | Fitz et al. |
| 9,020,788 B2 | 4/2015 | Lang |
| 9,023,050 B2 | 5/2015 | Lang et al. |
| 9,055,953 B2 | 6/2015 | Lang et al. |
| 9,060,788 B2 | 6/2015 | Bollinger |
| 9,066,728 B2 | 6/2015 | Burdulis, Jr. et al. |
| 9,072,531 B2 | 7/2015 | Fitz et al. |
| 9,084,617 B2 | 7/2015 | Lang et al. |
| 9,095,353 B2 | 8/2015 | Burdulis, Jr. et al. |
| 9,107,679 B2 | 8/2015 | Lang et al. |
| 9,107,680 B2 | 8/2015 | Fitz et al. |
| 9,113,921 B2 | 8/2015 | Lang et al. |
| 9,125,672 B2 | 9/2015 | Fitz et al. |
| 9,126,673 B1 | 9/2015 | Green et al. |
| 9,180,015 B2 | 11/2015 | Fitz et al. |
| 9,186,161 B2 | 11/2015 | Lang et al. |
| 9,186,254 B2 | 11/2015 | Fitz et al. |
| 9,211,199 B2 | 12/2015 | Ratron |
| 9,216,025 B2 | 12/2015 | Fitz et al. |
| 9,220,516 B2 | 12/2015 | Lang et al. |
| 9,220,517 B2 | 12/2015 | Lang et al. |
| 9,232,955 B2 | 1/2016 | Bonin, Jr. et al. |
| 9,237,950 B2 | 1/2016 | Hensley et al. |
| 9,241,724 B2 | 1/2016 | Lang et al. |
| 9,241,725 B2 | 1/2016 | Lang et al. |
| 9,278,413 B2 | 3/2016 | Sperling |

(56) References Cited

U.S. PATENT DOCUMENTS

| | | |
|---|---|---|
| 9,295,481 B2 | 3/2016 | Fitz et al. |
| 9,295,482 B2 | 3/2016 | Fitz et al. |
| 9,301,768 B2 | 4/2016 | Buza et al. |
| 9,308,005 B2 | 4/2016 | Fitz et al. |
| 9,308,053 B2 | 4/2016 | Bojarski et al. |
| 9,308,091 B2 | 4/2016 | Lang |
| 9,314,256 B2 | 4/2016 | Fitz et al. |
| 9,320,608 B2 | 4/2016 | Sperling |
| 9,320,620 B2 | 4/2016 | Bojarski et al. |
| 9,326,780 B2 | 5/2016 | Wong et al. |
| 9,333,085 B2 | 5/2016 | Fitz et al. |
| 9,351,743 B2 | 5/2016 | Kehres et al. |
| 9,358,018 B2 | 6/2016 | Fitz et al. |
| 9,381,025 B2 | 7/2016 | Fitz et al. |
| 9,381,026 B2 | 7/2016 | Trouilloud et al. |
| 9,387,083 B2 | 7/2016 | Al Hares et al. |
| 9,402,726 B2 | 8/2016 | Linderman et al. |
| 9,408,615 B2 | 8/2016 | Fitz et al. |
| 9,408,616 B2 | 8/2016 | Kehres et al. |
| 9,408,686 B1 | 8/2016 | Miller et al. |
| 9,414,928 B2 | 8/2016 | Sperling |
| 9,439,767 B2 | 9/2016 | Bojarski et al. |
| 9,486,226 B2 | 11/2016 | Chao |
| 9,495,483 B2 | 11/2016 | Steines et al. |
| 9,517,134 B2 | 12/2016 | Lang |
| 9,539,013 B2 | 1/2017 | Katrana et al. |
| 9,554,910 B2 | 1/2017 | Vanasse et al. |
| 9,575,931 B2 | 2/2017 | Ratron |
| 9,579,106 B2 | 2/2017 | Lo et al. |
| 9,579,110 B2 | 2/2017 | Bojarski et al. |
| 9,603,711 B2 | 3/2017 | Bojarski et al. |
| 9,636,229 B2 | 5/2017 | Lang et al. |
| 9,646,113 B2 | 5/2017 | Park et al. |
| 9,662,214 B2 | 5/2017 | Li et al. |
| 9,668,873 B2 | 6/2017 | Winslow et al. |
| 9,675,471 B2 | 6/2017 | Bojarski et al. |
| 9,681,956 B2 | 6/2017 | Al Hares et al. |
| 9,687,945 B2 | 6/2017 | Steines et al. |
| 9,700,420 B2 | 7/2017 | Fitz et al. |
| 9,700,971 B2 | 7/2017 | Lang |
| 9,713,533 B2 | 7/2017 | Taylor et al. |
| 9,715,563 B1 | 7/2017 | Schroeder |
| 9,717,508 B2 | 8/2017 | Iannotti et al. |
| 9,737,367 B2 | 8/2017 | Steines et al. |
| 9,741,263 B2 | 8/2017 | Iannotti et al. |
| 9,770,335 B2 | 9/2017 | Sperling |
| 9,775,680 B2 | 10/2017 | Bojarski et al. |
| 9,849,019 B2 | 12/2017 | Miller et al. |
| 9,872,773 B2 | 1/2018 | Lang et al. |
| 9,877,790 B2 | 1/2018 | Bojarski et al. |
| 9,895,230 B2 | 2/2018 | Mahfouz |
| 9,913,723 B2 | 3/2018 | Fitz et al. |
| 9,937,046 B2 | 4/2018 | Mahfouz |
| 9,943,370 B2 | 4/2018 | Asseln et al. |
| 9,956,047 B2 | 5/2018 | Bojarski et al. |
| 9,956,048 B2 | 5/2018 | Bojarski et al. |
| 9,993,341 B2 | 6/2018 | Vanasse et al. |
| 10,085,839 B2 | 10/2018 | Wong et al. |
| 2001/0047210 A1 | 11/2001 | Wolf |
| 2002/0007294 A1 | 1/2002 | Bradbury et al. |
| 2002/0082741 A1 | 6/2002 | Mazumder et al. |
| 2003/0139818 A1 | 7/2003 | Rogers et al. |
| 2004/0064189 A1 | 4/2004 | Maroney et al. |
| 2004/0102866 A1 | 5/2004 | Harris et al. |
| 2004/0133276 A1 | 7/2004 | Lang et al. |
| 2004/0171924 A1 | 9/2004 | Mire et al. |
| 2004/0181144 A1 | 9/2004 | Cinquin et al. |
| 2004/0243481 A1 | 12/2004 | Bradbury et al. |
| 2005/0049709 A1 | 3/2005 | Tornier |
| 2005/0065617 A1 | 3/2005 | Barrera et al. |
| 2005/0065628 A1 | 3/2005 | Roose |
| 2005/0098915 A1 | 5/2005 | Long et al. |
| 2005/0112397 A1 | 5/2005 | Rolfe et al. |
| 2005/0197814 A1 | 9/2005 | Aram |
| 2005/0216305 A1 | 9/2005 | Funderud |
| 2006/0136058 A1 | 6/2006 | Pietrzak |
| 2007/0089518 A1 | 4/2007 | Ericson et al. |
| 2007/0118055 A1 | 5/2007 | McCombs |
| 2007/0118243 A1 | 5/2007 | Schroeder et al. |
| 2007/0191741 A1 | 8/2007 | Tsai et al. |
| 2007/0244563 A1 | 10/2007 | Roche et al. |
| 2007/0249967 A1 | 10/2007 | Buly et al. |
| 2008/0014082 A1 | 1/2008 | Kunz et al. |
| 2008/0010900 A1 | 5/2008 | Maroney et al. |
| 2008/0183297 A1 | 7/2008 | Boileau et al. |
| 2008/0228269 A1 | 9/2008 | McLeod et al. |
| 2008/0243127 A1 | 10/2008 | Lang et al. |
| 2009/0226068 A1 | 9/2009 | Fitz et al. |
| 2009/0264894 A1 | 10/2009 | Wasielewski |
| 2009/0292464 A1 | 11/2009 | Fuchs et al. |
| 2010/0087927 A1 | 4/2010 | Roche et al. |
| 2010/0191100 A1 | 7/2010 | Anderson et al. |
| 2010/0217270 A1 | 8/2010 | Polinski et al. |
| 2010/0303313 A1 | 12/2010 | Lang et al. |
| 2011/0029088 A1 | 2/2011 | Raucher et al. |
| 2011/0035013 A1 | 2/2011 | Winslow et al. |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0119884 A1 | 5/2011 | Ratron |
| 2011/0137424 A1 | 6/2011 | Lappin et al. |
| 2012/0078258 A1 | 3/2012 | Lo et al. |
| 2012/0116203 A1 | 5/2012 | Vancraen et al. |
| 2012/0130434 A1 | 5/2012 | Stemniski |
| 2012/0141034 A1 | 6/2012 | Iannotti et al. |
| 2012/0143267 A1 | 6/2012 | Iannotti et al. |
| 2012/0253350 A1 | 10/2012 | Anthony et al. |
| 2012/0276509 A1 | 11/2012 | Iannotti et al. |
| 2012/0279933 A1 | 11/2012 | Hensler et al. |
| 2013/0053968 A1 | 2/2013 | Nardini et al. |
| 2013/0110116 A1 | 5/2013 | Kehres et al. |
| 2013/0110471 A1 | 5/2013 | Lang et al. |
| 2013/0114873 A1 | 5/2013 | Chaoui |
| 2013/0172898 A1 | 7/2013 | Iannotti et al. |
| 2013/0190882 A1 | 7/2013 | Humphrey |
| 2013/0211531 A1 | 8/2013 | Steines et al. |
| 2013/0261629 A1 | 10/2013 | Anthony et al. |
| 2013/0274752 A1 | 10/2013 | Trouilloud et al. |
| 2013/0338673 A1 | 12/2013 | Keppler |
| 2014/0039633 A1 | 2/2014 | Roche et al. |
| 2014/0257499 A1 | 9/2014 | Winslow et al. |
| 2014/0276867 A1 | 9/2014 | Kelley et al. |
| 2014/0371863 A1 | 12/2014 | Vanasse et al. |
| 2015/0045903 A1 | 2/2015 | Neal |
| 2015/0093283 A1 | 4/2015 | Miller et al. |
| 2015/0105787 A1 | 4/2015 | Tornier et al. |
| 2015/0150688 A1 | 6/2015 | Vanasse et al. |
| 2015/0223941 A1 | 8/2015 | Lang |
| 2015/0250552 A1 | 9/2015 | Radermacher et al. |
| 2015/0250597 A1 | 9/2015 | Lang et al. |
| 2015/0320430 A1 | 11/2015 | Kehres et al. |
| 2015/0328004 A1 | 11/2015 | Mafhouz |
| 2016/0015466 A1 | 1/2016 | Park et al. |
| 2016/0051367 A1 | 2/2016 | Gervasi et al. |
| 2016/0067049 A1 | 3/2016 | Flaherty et al. |
| 2016/0074052 A1 | 3/2016 | Keppler et al. |
| 2016/0100907 A1 | 4/2016 | Gomes |
| 2016/0120555 A1 | 5/2016 | Bonin, Jr. et al. |
| 2016/0143744 A1 | 5/2016 | Bojarski et al. |
| 2016/0143749 A1 | 5/2016 | Holovacs et al. |
| 2016/0157937 A1 | 6/2016 | Kehres et al. |
| 2016/0166392 A1 | 6/2016 | Vanasse et al. |
| 2016/0184104 A1 | 6/2016 | Sperling |
| 2016/0193051 A1 | 7/2016 | Budhabhatti et al. |
| 2016/0213385 A1 | 7/2016 | Iannotti et al. |
| 2016/0242933 A1 | 8/2016 | Deransart et al. |
| 2016/0256222 A1 | 9/2016 | Walch |
| 2016/0270854 A1 | 9/2016 | Chaoui et al. |
| 2016/0296285 A1 | 10/2016 | Chaoui et al. |
| 2016/0296290 A1 | 10/2016 | Furrer et al. |
| 2016/0324648 A1 | 11/2016 | Hodorek et al. |
| 2016/0331467 A1 | 11/2016 | Slamin et al. |
| 2016/0345987 A1 | 12/2016 | Guilloux et al. |
| 2016/0374697 A1 | 12/2016 | Kehres et al. |

(56) References Cited

U.S. PATENT DOCUMENTS

| | | | |
|---|---|---|---|
| 2017/0000614 A1 | 1/2017 | Mahfouz |
| 2017/0000615 A1 | 1/2017 | Mahfouz |
| 2017/0027587 A1 | 2/2017 | Fraone et al. |
| 2017/0027593 A1 | 2/2017 | Bojarski et al. |
| 2017/0056024 A1 | 3/2017 | Chao |
| 2017/0079803 A1 | 3/2017 | Lang |
| 2017/0105841 A1 | 4/2017 | Vanasse et al. |
| 2017/0105843 A1 | 4/2017 | Britton et al. |
| 2017/0112626 A1 | 4/2017 | Miller et al. |
| 2017/0119531 A1 | 5/2017 | Bojarski et al. |
| 2017/0151058 A1 | 6/2017 | Sperling |
| 2017/0216038 A1 | 8/2017 | Lang et al. |
| 2017/0231783 A1 | 8/2017 | Lang et al. |
| 2017/0249440 A1 | 8/2017 | Lang et al. |
| 2017/0258598 A1 | 9/2017 | Radermacher et al. |
| 2017/0273795 A1 | 9/2017 | Neichel et al. |
| 2017/0273800 A1 | 9/2017 | Emerick et al. |
| 2017/0273801 A1 | 9/2017 | Hodorek |
| 2017/0281357 A1 | 10/2017 | Taylor et al. |
| 2017/0296347 A1 | 10/2017 | Chua et al. |
| 2017/0304063 A1 | 10/2017 | Hatzidakis et al. |
| 2017/0360567 A1 | 12/2017 | Fitz et al. |
| 2017/0367766 A1 | 12/2017 | Mahfouz |
| 2017/0367828 A1 | 12/2017 | Steines et al. |
| 2017/0367834 A1 | 12/2017 | Fitz et al. |
| 2018/0028325 A1 | 2/2018 | Bojarski et al. |
| 2018/0161176 A1 | 6/2018 | Vivanz et al. |
| 2018/0228614 A1 | 8/2018 | Lang et al. |
| 2018/0235706 A1 | 8/2018 | Asseln et al. |
| 2018/0235762 A1 | 8/2018 | Radermacher et al. |
| 2018/0263782 A1 | 9/2018 | Lang et al. |
| 2018/0289380 A1 | 10/2018 | Mauldin et al. |
| 2019/0015113 A1 | 1/2019 | Morvan |
| 2019/0015116 A1 | 1/2019 | Neichel et al. |
| 2019/0015117 A1 | 1/2019 | Neichel et al. |
| 2019/0015118 A1 | 1/2019 | Neichel et al. |
| 2019/0015119 A1 | 1/2019 | Athwal et al. |
| 2019/0015221 A1 | 1/2019 | Neichel et al. |
| 2019/0038360 A1 | 2/2019 | Chaoui |

FOREIGN PATENT DOCUMENTS

| | | | |
|---|---|---|---|
| CA | 2938709 | | 5/2015 |
| EP | 1 249 213 | | 10/2002 |
| EP | 1 265 555 | | 12/2002 |
| EP | 1 563 810 | | 8/2005 |
| EP | 1 862 151 | | 12/2007 |
| EP | 1 902 689 | | 3/2008 |
| EP | 1 952 788 | | 8/2008 |
| EP | 2 135 576 | | 12/2009 |
| EP | 1 917 051 | B1 | 6/2010 |
| EP | 2 243 445 | | 10/2010 |
| EP | 2 324 801 | A1 | 5/2011 |
| EP | 2 501 313 | | 9/2012 |
| EP | 2 544 601 | | 1/2013 |
| EP | 2583242 | | 4/2013 |
| EP | 2 845 547 | | 3/2015 |
| EP | 2 965 720 | | 1/2016 |
| EP | 3057518 | | 8/2016 |
| EP | 3057524 | | 8/2016 |
| EP | 3065671 | | 9/2016 |
| EP | 3068317 | | 9/2016 |
| EP | 2 874 570 | B1 | 1/2017 |
| EP | 3 117 801 | | 1/2017 |
| FR | 2 579 454 | | 10/1986 |
| FR | 2 859 099 | | 3/2005 |
| FR | 2962573 | A1 | 1/2012 |
| FR | 2982694 | B1 | 11/2016 |
| FR | 2982979 | B1 | 11/2016 |
| FR | 2982693 | B1 | 12/2016 |
| GB | 2501494 | A | 10/2013 |
| WO | WO 93/025157 | | 12/1993 |
| WO | WO 00/35346 | | 6/2000 |
| WO | WO 00/59411 | | 10/2000 |
| WO | WO 02/061688 | | 8/2002 |
| WO | WO 2010/120346 | | 10/2010 |
| WO | WO 2011/110374 | | 9/2011 |
| WO | WO 2011/154891 | | 12/2011 |
| WO | WO 2011/157961 | | 12/2011 |
| WO | WO 2012/021241 | | 2/2012 |
| WO | WO 2012/058349 | | 5/2012 |
| WO | WO 2012/125319 | | 9/2012 |
| WO | WO 2013/060851 | | 5/2013 |
| WO | WO 2013/062848 | | 5/2013 |
| WO | WO 2013/062851 | | 5/2013 |
| WO | WO-2013060851 A * | 5/2013 ......... A61B 17/1778 |
| WO | WO 2013/142998 | | 10/2013 |
| WO | WO 2014/020561 | | 2/2014 |
| WO | WO 2014/035991 | | 3/2014 |
| WO | WO 2014/180972 | | 11/2014 |
| WO | WO 2015/052586 | | 4/2015 |
| WO | WO 2015/056097 | | 4/2015 |
| WO | WO 2015/068035 | | 5/2015 |
| WO | WO 2015/071757 | | 5/2015 |
| WO | WO 2015/175397 | | 11/2015 |
| WO | WO 2015/185219 | | 12/2015 |
| WO | WO 2017/091657 | | 6/2017 |
| WO | WO 2017/105815 | | 6/2017 |
| WO | WO 2017/106294 | | 6/2017 |
| WO | WO 2017/184792 | | 10/2017 |
| WO | WO 2017/214537 | | 12/2017 |
| WO | WO 2018/022227 | | 2/2018 |
| WO | WO 2019/014278 | | 1/2019 |
| WO | WO 2019/014281 | | 1/2019 |
| WO | WO 2019/033037 | | 2/2019 |

OTHER PUBLICATIONS

Boileau, et al., "The three-dimensional geometry of the proximal humerus: implications for surgical technique and prosthetic design." The Journal of bone and joint surgery. British vol. 79.5 (1997): 857-865.

Habets, et al., Computer assistance in orthopaedic surgery. Technische Universiteit Eindhoven, 2002.

Hempfing, et al. "Surgical landmarks to determine humeral head retrotorsion for hemiarthroplasty in fractures." Journal of shoulder and elbow surgery 10.5 (2001): 460-463.

Ma, et al., "Robust registration for computer-integrated orthopedic surgery: laboratory validation and clinical experience." Medical image analysis 7.3 (2003): 237-250.

"Olympia Total Shoulder System Surgical Technique", Wright Medical Technology, 2001, in 19 pages.

Radermacher, K., et al., "Computer Assisted Orthopaedic Surgery with Image Based Individual Templates," Clinical Orthopaedics and Related Research, No. 354, Sep. 1998, pp. 28-38.

Radermacher, K., et al., "Image Guided Orthopedic Surgery Using Individual Templates: Experimental Results and Aspects of the Development of a Demonstrator for Pelvis Surgery", Health Care Sector, Telematics Applications Program, 1997, pp. 606-615.

Tornier, "Salto Talaris, Total Ankle Prosthesis", 2009.

Valstar, et al. "Towards computer-assisted surgery in shoulder joint replacement." ISPRS journal of photogrammetry and remote sensing 56.5-6 (2002): 326-337.

Valstar, et al. "The use of Roentgen stereophotogrammetry to study micromotion of orthopaedic implants." ISPRS journal of photogrammetry and remote sensing 56.5-6 (2002): 376-389.

Welsh, et al., "CT-based preoperative analysis of scapula morphology and glenohumeral joint geometry." Computer Aided Surgery 8.5 (2003): 264-268.

Zimmer, "Zimmer ® PSI Shoulder Trabecular Metal™ Reverse Glenoid Base Plate Surgical Technique", Dec. 30, 2013.

Extended European Search Report issued in EP Application No. 18187134.4, dated Nov. 22, 2018 in 6 pages.

International Search Report and Written Opinion for PCT/IB2014/002711 dated Mar. 23, 2015 in 12 pages.

Dougherty, "Digital Image Processing for Medical Applications," May 11, 2009 (May 11, 2009), Cambridge University Press, XP002615721.

(56) References Cited

OTHER PUBLICATIONS

Gregory, et al.," Accuracy of Glenoid Component Placement in Total Shoulder Arthroplasty and Its Effect on Clinical and Radiological Outcome in a Retrospective, Longitudinal, Monocentric Open Study," PLOS One, p. e75791, Aug. 1, 2013, vol. 8, No. 10.
Iannotti et al., "Prosthetic positioning in total shoulder arthroplasty," Journal of Shoulder and Elbow Surgery, Jan. 1, 2005, vol. 14, No. 1S, pp. S111-S121.
Kobashi et al., "Knowledge-Based Organ Identification from CT Images," Pattern Recognition, Elsevier, GB, vol. 28, No. 4, Apr. 1, 1995 (Apr. 1, 1995), pp. 475-491, XP004013165.
Lee, C.C. et al., "Identifying multiple abdominal organs from CT image series using a multimodule contextual neural network and spatial fuzzy rules", IEEE Transactions on Information Technology in Biomedicine, IEEE Services Center, Los Alamitos, CA, US, vol. 7, No. 3, Sep. 1, 2003 (Sep. 1, 2003) pp. 208-217, XP011100536.
Wu, et al. "An interface for the data exchange between CAS and CAD/CAM systems." International Congress Series. Vol. 1256. Elsevier, 2003.

* cited by examiner

SHOULDER PATIENT SPECIFIC INSTRUMENT

INCORPORATION BY REFERENCE TO ANY PRIORITY APPLICATIONS

The present application is a divisional of U.S. application Ser. No. 15/024,747, filed Mar. 24, 2016, which is a national phase of PCT Application No. PCT/IB2014/002711, filed Nov. 11, 2014, which claims priority benefit under 35 U.S.C. § 119(e) to U.S. Provisional Patent Application Ser. No. 61/903,814, filed Nov. 13, 2013, both of which are incorporated by reference in their entirety herein. Any and all applications for which a foreign or domestic priority claim is identified in the Application Data Sheet as filed with the present application are hereby incorporated by reference under 37 CFR 1.57.

BACKGROUND

1. Field of the Invention

The present invention relates to shoulder implants. In particular, the present invention relates to glenoid implants for shoulder joints having scapula erosion and devices that facilitate implanting the same.

2. Description of the Related Art

In a healthy shoulder joint, the head of the humerus interacts with the glenoid cavity of the scapula to form a "ball and socket" joint. The humeral head abuts and articulates with the glenoid to provide a wide range of motion. In an unhealthy shoulder joint, the interaction between the glenoid and the humerus is compromised, requiring repair or replacement.

Replacing the glenoid articular surface of the scapula of a human with a prosthetic glenoid component is a delicate surgical operation, notably because of the muscular environment of the shoulder. It is found that, depending on the position of implantation of such a glenoid component, risks of separation of the component from the underlying scapula exist due to forces applied to this component in subsequent movements of the prosthesized shoulder. In particular, in certain patients, it was found that, even if the implantation on their scapula of such a glenoid component was perfectly centered on the articular head of the corresponding humerus on completion of the surgical implantation operation, the resumption of their activities led, more or less rapidly, to instability of the prosthesis.

Currently, several companies are working on custom devices to guide glenoid bone preparation. One example filed by Tornier, Inc. is U.S. patent application Ser. No. 12/954,423, filed 24 Nov. 2010 and published as US 2011/0130795 A1.

SUMMARY

A patient specific glenoid guide is provided to facilitate properly aligned implantation of a glenoid prosthesis into a patient. The guide shape is designed preoperatively based on the unique configuration of the scapula of the patient. The guide orientation is chosen preoperatively based on one or more of the bone structure of the patient, the wear pattern of the patient's glenoid cavity, the anchoring means of the glenoid prosthesis, or other aspects.

The guide may reversibly snap into securement with the scapula of the patient to hold the guide to the scapula during surgery. The guide may establish one or more axes through the shoulder joint about which subsequent bone preparation procedures and prosthesis implantation may be carried out. The guide may allow insertion of one or more K-wires or pins through the guide and into the scapula along the axis, and also allow removal of the guide without removing the one or more K-wires or pins.

The patient specific glenoid guide may be comprised of a central tubular element and three or more peripheral arms emanating from the central tubular element. One or more arms may terminate in a peripheral peg. One or more peripheral peg may be configured to reversibly engage with the scapula of the patient. The guide may be made by rapid prototyping or three dimensional printing methods.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION OF THE PREFERRED EMBODIMENT

Figure 1:
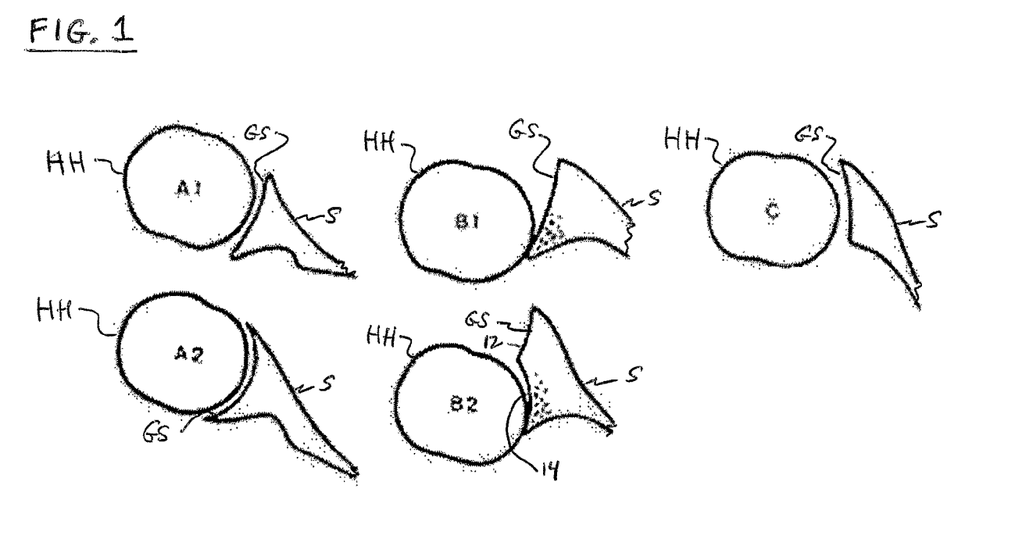
FIG. 1 illustrates schematic views of worn shoulder joints.

FIG. 1 illustrates five examples of worn shoulder joints that can be found in patients in need of shoulder arthroplasty. Each joint is comprised of a humeral head HH and a scapula S. The glenoid joint surface GS of the scapula is worn and can be classified as A1, A2, B1, B2, or C according to the shape of the glenoid surface ("Glenoid morphology in OA: Watch Classification", Walch G. et. al., J. Arthroplasty, 14:756-760, 1999). A glenoid GS may include a neo-glenoid portion 14 that has a significant amount of erosion and a paleo-glenoid portion 12 that has little or no erosion. Such a glenoid is commonly referred to as a "type-B2" glenoid (J. Bone Joint Surg. Br. 2011 vol. 93-B no. SUPP IV, 571). A prosthetic glenoid component (not shown) can be adapted to be positioned between the scapula and the humeral component. The glenoid component is also adapted to articulate with the humeral component. The humeral component may be a humeral prosthesis secured to the humerus of the subject or an anatomical humeral head of the subject.

As part of the process for restoring a functional articular surface to the scapula a glenoid implant is firmly attached to the scapula by a fixation means (not shown). In some examples the fixation means comprises one or more screws, pegs, keels, fins, cement, or other fixation means. It is desirable to establish proper orientation of the glenoid implant in relation to the scapula and the humerus to assure that the fixation means has adequate strength to resist implant dislodgement from forces generated by articular motions of the joint. For example, screws must have adequate pull-out strength to resist articular forces of the joint that tend to dislodge the implant from the shoulder bones. Further, proper orientation of the glenoid implant in relation to the scapula and the humerus can minimize the forces generated on the glenoid implant during articulation of the shoulder joint. To facilitate proper orientation of the glenoid implant an axis through the shoulder joint can be established and the axis used to properly orient the glenoid implant so as to accomplish the above goals.

Another part of the process for properly fitting a glenoid implant to the scapula can be preparing the worn surface of the scapula so that the prepared surface will match a previously prepared surface of the glenoid implant. A surgeon may need to remove a significant amount of bone including cortical bone of the relatively healthy portions of the glenoid to accommodate typical glenoid implants. When these matched surfaces are brought into apposition the combination will resist rocking, sliding, twisting, and other articular motions of the joint that tend to dislodge the implant from the shoulder bones. To facilitate proper orientation of the glenoid implant an axis through the shoulder joint can be established and the axis used to guide scapula surface preparation tools such as reamers, guides, broaches and other devices so as to accomplish the above goals.

Figure 2:
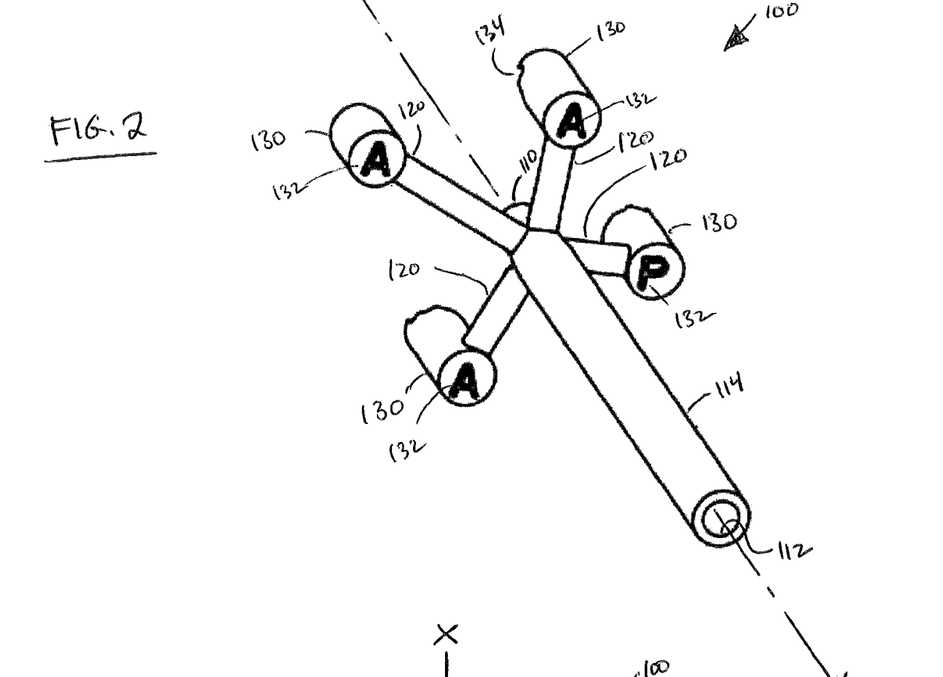
FIG. 2 illustrates an isometric plan view of a patient specific glenoid guide.
Figure 3:
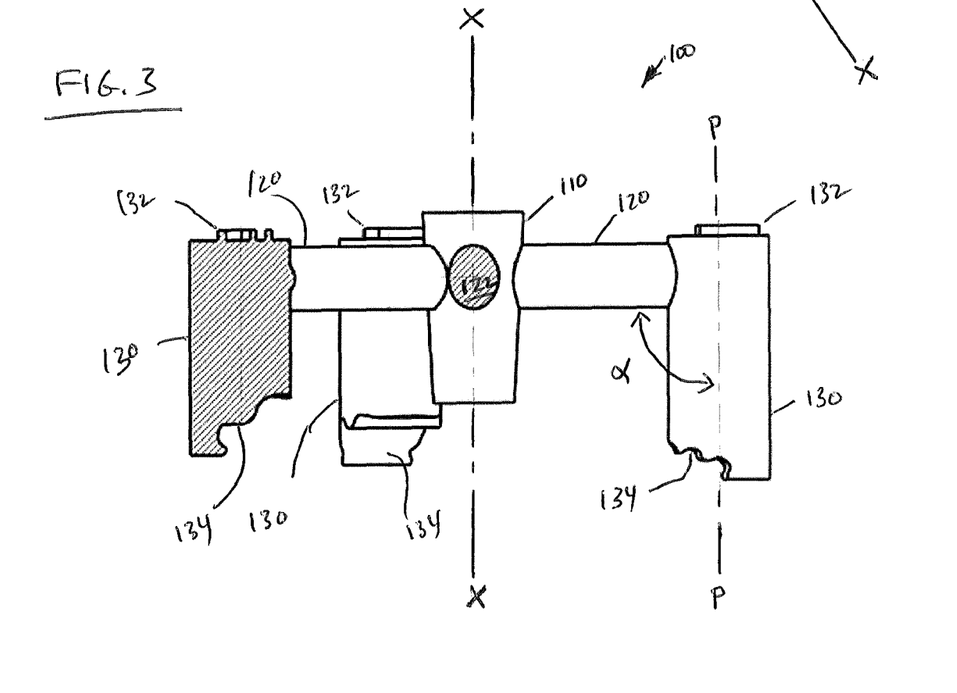
FIG. 3 illustrates a partial cross sectional side view of a patient specific glenoid guide.

FIGS. 2 and 3 illustrate one embodiment of a patient specific glenoid guide. Guide 100 is a unique structure based on the exact shoulder joint anatomy of a specific patient. Guide 100 is comprised of central tubular element 110, three or more arms 120, and at least three arms each having peripheral peg 130.

Central tubular element 110 is comprised of lumen 112 having axis X-X and is designed to guide a drill bit (not shown) for drilling a hole in the scapula. In another embodiment central tubular element 110 is designed to guide an alignment pin (not shown) through lumen 112 along axis X-X.

Figure 4A:
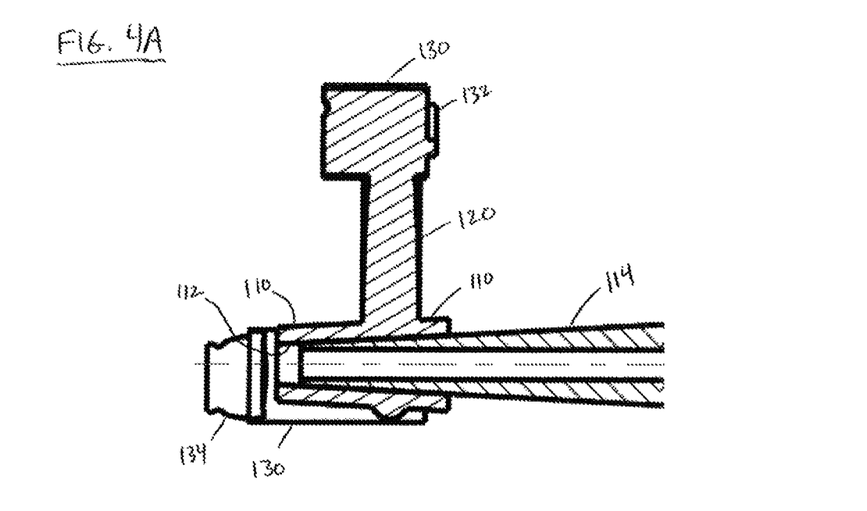
FIG. 4A illustrates a partial cross sectional side view of a patient specific glenoid guide.
Figure 4B:
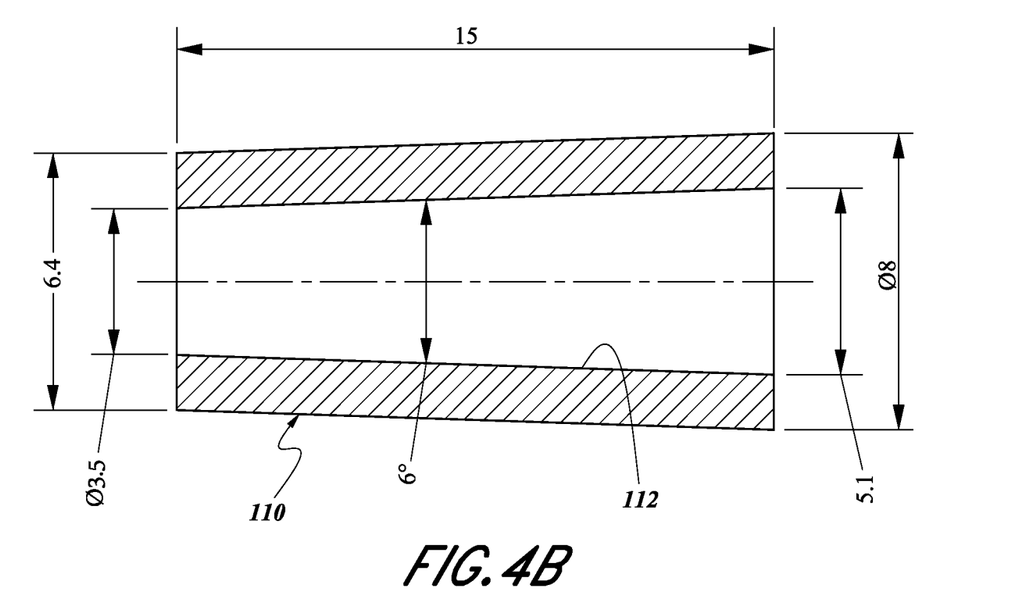
FIG. 4B illustrates a cross sectional side view of a portion of a patient specific glenoid guide.

In a further embodiment (see FIGS. 4A and 4B) guide 100 is used with commercially available metallic pin guide 114 of a generic design that is not patient specific. Pin guide 114 can be engaged with lumen 112 of central tubular element 110 to hold the two components together during surgery. In one embodiment pin guide is engaged with central tubular element by friction fit. In another embodiment pin guide is engaged with central tubular element by locking conical tapers, in one example Morse tapers. Specific dimensions (in mm) of central tubular element 110 for one locking taper embodiment are illustrated in FIG. 4B, and pin guide 114 external mating dimensions are the same as the internal mating dimensions of the central tubular element. Typically pin guide 114 is long enough to function as a handle during surgery for placement of guide 100.

At least three arms 120 are provided on the guide, four arms are preferred, and 5, 6, 7, or 8 arms are contemplated. The arms between the central tubular element and each peripheral peg may have an elliptical, round, ovoid, polygonal, square, rectangular, triangular, other cross-section. In one embodiment the arm has an elliptical cross section and the major axis of the ellipse is perpendicular to the glenoid surface, the major axis is about 5 mm in length and the minor axis is about 4 mm in length. Arm 120 has a cross sectional area 122. Arm cross sectional areas of 10 square millimeters to 40 square millimeters and any cross sectional area therebetween are contemplated.

Peripheral peg 130 is comprised of identifier 132 and engagement surface 134. At least three pegs are provided on the guide, four pegs are preferred, and 5, 6, 7, or 8 pegs are contemplated. Three pegs are positioned to engage the anterior border of the glenoid cavity while one peg is positioned to engage the supero-posterior border of the glenoid cavity. Opposite to peg engagement surface 134, on the peg lateral extremity, the pegs are marked with identifier 132. In some embodiments anterior pegs are marked with identifier "A" while posterior pegs are marked with identifier "P". Peg diameters of 6 mm to 10 mm and any diameter therebetween are contemplated. In one embodiment peg diameter is 8 mm. In another embodiment the posterior peg axis P-P is angled at an obtuse angle $\alpha$ from the arm so as to not be in conflict with the posterior retractor during the arthroplasty procedure. Engagement surface 134 may be customized to closely conform to the 3 dimensional shape of the border of the glenoid cavity.

Figure 6:
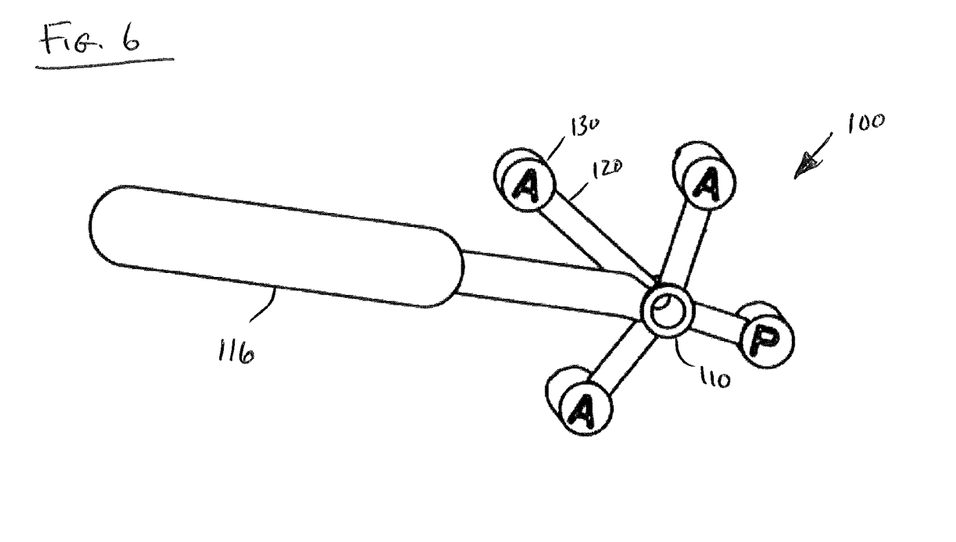
FIG. 6 illustrates an isometric plan view of an alternate embodiment of a patient specific glenoid guide.

Patient specific glenoid guide 100 optionally comprises handle 116 (FIG. 6). Handle 116 is long enough to function as a handle during surgery for placement of guide 100. Also, use of handle 116 instead of pin guide 114 for manipulation of guide 100 allows a short drill bit to be used through central tubular element 110 rather than a long drill bit through the combination of central tubular element 110 plus drill guide 114.

Figure 7:
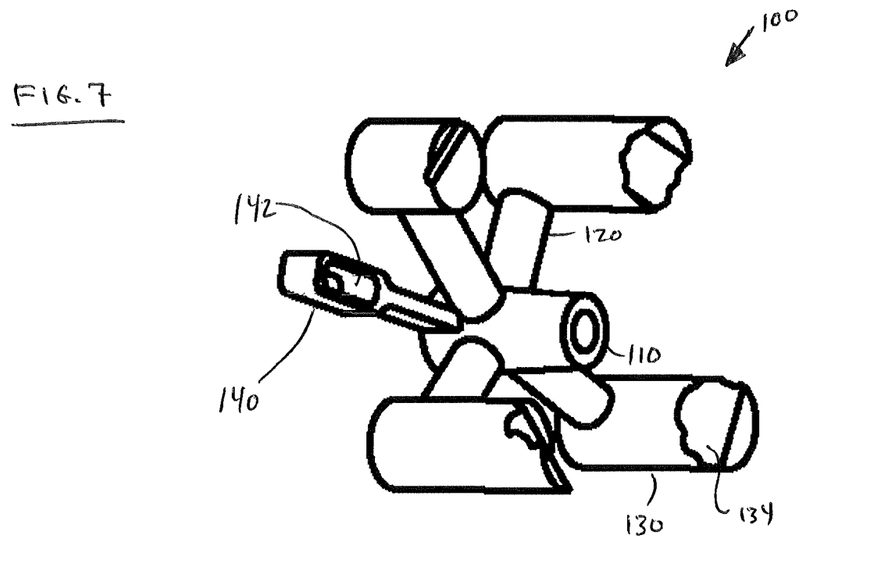
FIG. 7 illustrates an isometric bottom view of an alternate embodiment of a patient specific glenoid guide.

Patient specific glenoid guide 100 optionally comprises strut 140 having slot 142 (FIG. 7). The slot rotational position along the central axis X-X of the guide is the one of the supero-inferior axis of the glenoid component as determined by the pre-operative planning. Slot 142 is optionally used by the surgeon to mark this axis on the patient's bone with electrocautery.

In a further embodiment (not shown), second guide 100' is associated with first guide 100. Second guide 100' is similar to first guide 100 except that second guide 100' is designed to fit the patient's scapula after the scapula shape has been modified, for example, modified by reaming, and central tubular element 110' is comprised of two or more lumens 112', 112" having axes parallel to axis X-X. In some embodiment's lumens 112', 112" may be used to guide a drill bit (not shown) for drilling at least 2 holes in the scapula.

Guide 100 can be made by molding, machining, casting, thermal forming, or by other methods. In one embodiment guide 100 is made by rapid prototyping techniques, additive manufacturing or three dimensional printing using methods such as stereolithography or laser sintering. Guide 100 can be comprised of thermoplastics such as polyamide (such as PA2200 by Arptech) or metals such as titanium or stainless steel, or other materials.

Guide 100 is designed from three dimensional (3D) data about the anatomy of a patient's shoulder. The position and orientation of the axis X-X of the central tubular element 110 is defined according to pre-operative planning. The design process reproduces the translational positions of the glenoid component on three axes, (the antero-posterior axis, the supero-inferior axis and the medio-lateral axis) and it also reproduces the rotational positions of the glenoid component around the same three axes (supero—inferior axis (version), antero-posterior axis (inclination), and the medio-lateral axis (rotation)). By visualizing all of these positions a best choice position and orientation of axis X-X can be selected before operating on the patient. Also, a variety of glenoid implants can be evaluated for compatibility and performance in relation to the patients specific anatomy.

Figure 5:
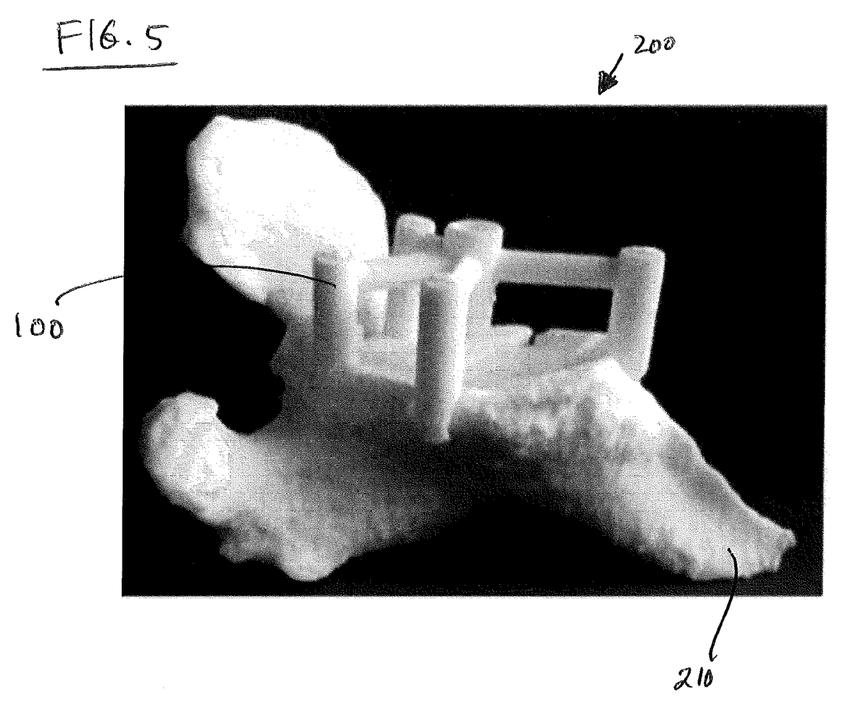
FIG. 5 illustrates an isometric plan view of a patient specific glenoid guide attached to a model of a patient's scapula.

In one exemplar embodiment a three dimensional model of the patients shoulder is generated from imaging data obtained using a medical imaging technique such as a CT scan or a MRI. The imaging data are processed manually or automatically to generate a 3D model of the patient's scapula. From the 3D model of the patient's scapula, patient-specific guide 100 is designed automatically or manually using various CAD programs and/or software available such as Solid Works or ProEngineer.

a. As a first step in this example the 3D model of the bone is displayed in a specific environment in which the surgeon is able to select the desired implant and to place it at the desired location and desired orientation in the 3D model of the patient's scapula. Alternatively the implant could be automatically selected and/or placed based on a set of pre-determined criteria such as those described in EP2324801A1 or US2011/0119884 A1 which are incorporated herein in their entirety and can be found in the Appendix.

b. As a second step in this example, once the implant is selected and placed in position in the 3D model of the patient's scapula the location of the pegs is determined by the surgeon or by an engineer. Then the guide structure, including central tubular element 110, arms 120, pegs 130, and all of their features as described above, is manually or automatically generated. A dilatation of 2 pixels of the outside dimensions of the scapula is applied to bone model, and therefore to the guide engagement surface, in order to get a proper fit between the guide and the bone model as well as between the guide and the native bone.

c. The patient-specific guide 100 so generated will have a three dimensional engagement surface at the distal end of each peg that is complementary and made to conformingly contact the anatomical surface of the glenoid cavity border. The patient-specific guide 100 is thereby configured to fit at a unique position to the anatomical surface of the scapula. The central element of the guide so generated is in the proper location and orientation for proper location of the glenoid implant.

d. Optionally a 3D bone model 210 of the patient's scapula can be produced from the 3D imaging data, and said model can be provided to the surgeon with guide 100 as part of an implant kit 200 (FIG. 5). Such a model will allow the surgeon to test the fit and orientation of the guide 100 against the model of the patient's scapula prior to surgery, and can be a reference for the surgeon during surgery.

A non-limiting exemplar method of use of the patient specific glenoid guide is now described.

a. A patient undergoes a medical imaging technique such as a CT scan or a MRI and the imaging datum are processed manually or automatically to generate a 3D model of the patient's scapula.

b. The 3D model of the scapula is displayed in a specific environment in which the surgeon selects the desired implant and places it at the desired location and desired orientation in the 3D model of the patient's scapula. Alternatively the implant is automatically selected and/or placed based on a set of pre-determined criteria such as those described in EP2324801A1 or US2011/0119884 A1 which are incorporated herein in their entirety and can be found in the Appendix.

c. The location of 4 pegs is determined by the surgeon or by an engineer.

d. The guide structure, including central tubular element 110, arms 120, pegs 130, and all of their features as described above, is manually or automatically generated. A dilatation of 2 pixels of the outside dimensions of the scapula is applied to bone model, and therefore to the guide engagement surface, in order to get a proper fit between the guide and the bone model as well as between the guide and the native bone.

e. Optionally a 3D bone model of the patient's scapula is produced from the 3D imaging data.

f. The glenoid guide is provided to the surgeon. Optionally, a kit comprised of the 3D bone model and glenoid guide is provided to the surgeon.

g. The surgeon exposes the glenoid cavity of the patient.

h. The glenoid guide is pressed onto the border of the glenoid cavity and engages the glenoid in a snap fit attachment.

i. Pin placement through lumen 112 of guide 110 into patients scapula is performed.

j. Guide 110 is removed from the pin.

k. Scapula surface preparation and/or glenoid prosthesis placement is performed using pin as a guide.

l. Pin is removed.

m. Remainder of shoulder arthroplasty procedure is completed.

Terminology

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The term "about" as used herein represent an amount close to the stated amount that still performs a desired function or achieves a desired result. For example, the term "about" may refer to an amount that is within less than 10% of the stated amount, as the context may dictate.

Any methods disclosed herein need not be performed in the order recited. The methods disclosed herein include certain actions taken by a practitioner; however, they can also include any third-party instruction of those actions, either expressly or by implication. For example, actions such as "positioning three pegs around an anterior anatomical feature adjacent of the a glenoid cavity" include "instructing the positioning of three pegs around an anterior anatomical feature adjacent of the a glenoid cavity."

Although certain embodiments and examples have been described herein, it will be understood by those skilled in the art that many aspects of the glenoid guide shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

EXAMPLE EMBODIMENTS

The following example embodiments identify some possible permutations of combinations of features disclosed herein, although other permutations of combinations of features are also possible.

1. A patient specific glenoid guide for attachment to a scapula of a patient, the glenoid guide comprising:
   a guide feature;
   at least three arms having a first end coupled with the guide feature and a second end disposed away from the guide feature; and
   at least three peripheral pegs, each peripheral peg extending from the second end of a corresponding arm and comprising an engagement surface;
   wherein the engagement surface is configured to engage the scapula of the patient to provide a snap fit attachment onto the scapula.

2. The patient specific glenoid guide of Embodiment 1, wherein the guide feature comprises a central tubular element that comprises a lumen.

3. The patient specific glenoid guide of Embodiment 1 or 2, wherein the guide feature is tapered.

4. The patient specific glenoid guide of any one of Embodiments 1 to 3, wherein the guide feature is configured to receive a pin guide.

5. The patient specific glenoid guide of any one of Embodiments 1 to 4, wherein the at least three peripheral pegs comprises four peripheral pegs.

6. The patient specific glenoid guide of Embodiment 5, wherein three of the four peripheral pegs are configured to engage an anterior anatomical feature of the scapula, and wherein one of the four peripheral pegs is configured to engage a supero-posterior anatomical feature of the scapula.

7. The patient specific glenoid guide of Embodiment 6, wherein three of the four peripheral pegs are configured to engage an anterior border of a glenoid cavity, and wherein one of the four peripheral pegs is configured to engage a supero-posterior border of the glenoid cavity.

8. The patient specific glenoid guide of any one of Embodiments 1 to 7, wherein each of the at least three arms comprises an elliptical cross section, the major axis of the elliptical cross-section being perpendicular to a glenoid cavity when the glenoid guide is coupled with the scapula.

9. The patient specific glenoid guide of any one of Embodiments 1 to 8, wherein an angle between one of the at least three arms and a corresponding peg is an obtuse angle.

10. The patient specific glenoid guide of any one of Embodiments 1 to 9, further comprising a lateral handle extending laterally from the guide feature.

11. The patient specific glenoid guide of any one of Embodiments 1 to 10, further comprising a strut extending laterally from the guide feature, the strut comprising a slot.

12. A system for guiding a glenoid prosthesis, the system comprising:
   the glenoid guide of any one of Embodiments 1 to 11; and
   a pin guide configured to engage the guide feature.

13. The system of Embodiment 12, wherein the pin guide comprises a tapered surface, and wherein the guide feature is tapered to receive the tapered pin guide.

14. A surgical kit comprising:
   a patient specific glenoid guide, the glenoid guide comprising:
   a guide feature;
   a plurality of arms extending from the guide feature; and
   a plurality of peripheral pegs, each of the plurality of peripheral pegs extending from a corresponding arm, each of the plurality of peripheral pegs comprising an engagement surface; and
   a three dimensional model of a patient's scapula comprising a glenoid cavity border; and
   wherein the engagement surfaces of the patient specific glenoid guide are configured to engage the glenoid cavity border of the model by a snap fit.

15. The surgical kit of Embodiment 14, wherein the guide feature comprises a central tubular element that comprises a lumen.

16. The surgical kit of Embodiment 14 or 15, wherein the guide feature is tapered.

17. The surgical kit of any one of Embodiments 14 to 16, wherein the u feature is configured to receive a pin guide.

18. The surgical kit of any one of Embodiments 14 to 17, wherein the plurality of peripheral pegs comprises four peripheral pegs.

19. The surgical kit of Embodiment 18, wherein three of the four peripheral pegs are configured to engage an anterior portion of the glenoid cavity border, and wherein one of the four peripheral pegs is configured to engage a supero-posterior portion of the glenoid cavity border.

20. The surgical kit of any one of Embodiments 14 to 19, wherein each of the plurality of arms comprises an elliptical cross section, the major axis of the elliptical cross-section being perpendicular to a portion of the model corresponding to a glenoid cavity when the guide is applied to the model.

21. The surgical kit of any one of Embodiments 14 to 20, wherein an angle between one of the plurality of peripheral pegs and the corresponding arms is an obtuse angle.

22. The surgical kit of any one of Embodiments 14 to further comprising a. lateral handle extending laterally from the guide feature.

23. The surgical kit of any one of Embodiments 14 to 22, further comprising a. strut extending laterally from the guide feature, the strut comprising a slot.

24. The surgical kit of any one of Embodiments 14 to 23, further comprising a. pin guide coupled to the guide feature.

25. A method of guiding a glenoid prosthesis, the method comprising:
pre-operatively determining a position and an orientation of guide feature of a glenoid guide based on a specific patient's scapula, the glenoid guide comprising:
a plurality of arms extending from the guide feature; and
a peripheral peg extending from each of the plurality of arms, the guide feature disposed inward of the peripheral pegs;
engaging the glenoid guide with the scapula;
inserting a pin having an axis through the guide feature to or through the scapula. 26. The method of Embodiment 25, wherein the guide feature comprises a central tubular element that comprises a lumen and inserting the pin comprises inserting the pin through the lumen of the guide feature.

27. The method of Embodiment 25 or 26, wherein engaging the glenoid guide with the scapula comprises engaging the glenoid guide with a glenoid cavity border by snap fit.

28. The method of any one of Embodiments 25 to 27, wherein engaging the glenoid guide with the scapula comprises positioning three pegs around an anterior anatomical feature of a glenoid cavity and positioning one peg at a supero-posterior anatomical feature of the glenoid cavity.

29. The method of Embodiment 28, wherein engaging the glenoid guide with the scapula comprises positioning three pegs around an anterior anatomical border of the glenoid cavity and positioning one peg at a supero-posterior border of the glenoid cavity.

30. The method of any one of Embodiments 2.5 to 29, further comprising advancing the glenoid prosthesis along the pin.

31. The method of any one of Embodiments 2.5 to 30, further comprising securing the pin to the guide feature by a friction fit.

32. The method of any one of Embodiments 25 to 30, further comprising securing a conical taper of the pin with a conical taper of the guide feature.

What is claimed is:

1. A patient specific glenoid guide for attachment to a scapula of a patient, the guide comprising:
a guide feature;
at least three arms having a first end coupled with the guide feature and a second end disposed away from the guide feature;
at least three peripheral pegs, each peripheral peg extending from the second end of a corresponding arm and comprising an engagement surface configured to engage the scapula of the patient; and
a strut extending laterally from the guide feature, the strut comprising a positioning opening.

2. The patient specific glenoid guide of claim 1, wherein the positioning opening is provided to be positioned in use along a supero-inferior axis of a glenoid component to be implanted with reference to the guide.

3. The patient specific glenoid guide of claim 1, wherein the guide feature comprises a tubular element having a lumen.

4. The patient specific glenoid guide of claim 3, wherein a position and orientation of the tubular element is provided to control a translational and rotational position of the glenoid component during implantation.

5. The patient specific glenoid guide of claim 4, wherein the position and orientation of the tubular element provides translational control along an axis.

6. The patient specific glenoid guide of claim 3, wherein the tubular element is a central tubular element.

7. The patient specific glenoid guide of claim 1, wherein the guide is configured so that one or more pins are insertable through the guide to establish one or more axes about which subsequent bone preparation procedures may be carried out.

8. The patient specific glenoid guide of claim 1, wherein the guide feature comprises two or more lumens having parallel axes.

9. The patient specific glenoid guide of claim 1, wherein the guide feature comprises a tapered lumen.

10. The patient specific glenoid guide of claim 1, wherein the guide feature is configured to receive a pin guide.

11. The patient specific glenoid guide of claim 1, wherein the at least three peripheral pegs comprises four peripheral pegs.

12. The patient specific glenoid guide of claim 11, wherein three of the four peripheral pegs are configured to engage an anterior anatomical feature of the scapula, and wherein one of the four peripheral pegs is configured to engage a supero-posterior anatomical feature of the scapula.

13. The patient specific glenoid guide of claim 11, wherein three of the four peripheral pegs are configured to engage an anterior border of a glenoid cavity, and wherein one of the four peripheral pegs is configured to engage a supero-posterior border of the glenoid cavity.

14. The patient specific glenoid guide of claim 1, wherein the positioning opening comprises a slot.

15. A patient specific glenoid guide for attachment to a scapula of a patient, the glenoid guide comprising: a guide feature configured to receive a pin guide; a plurality of arms having a first end coupled with the guide feature and a second end disposed away from the guide feature; a plurality of pegs, each peripheral peg extending from the second end of a corresponding arm and comprising an engagement surface configured to conform to a three dimensional shape of a glenoid cavity border of the scapula of the patient, wherein the guide feature comprises a tapered lumen configured to receive the pin guide.

16. The patient specific glenoid guide of claim 15, wherein the engagement surface is configured to engage the scapula of the patient to provide a snap fit attachment onto the scapula.

17. The patient specific glenoid guide of claim 15, wherein the plurality of arms comprises at least three arms.

18. The patient specific glenoid guide of claim 15, further comprising two or more lumens having parallel axes.

19. The patient specific glenoid guide of claim 15, further comprising a strut extending laterally from the guide feature.

20. The patient specific glenoid guide of claim 19, wherein the strut comprises a positioning opening.

21. The patient specific glenoid guide of claim 15, wherein the guide feature is configured to directly receive a drill bit.

22. The patient specific glenoid guide of claim 21, further comprising a handle.

23. The patient specific glenoid guide of claim 15, further comprising the pin guide, the pin guide comprising a lumen configured to receive a drill bit.

\* \* \* \* \*

UNITED STATES PATENT AND TRADEMARK OFFICE
CERTIFICATE OF CORRECTION

| | |
|---|---|
| PATENT NO. | : 11,179,249 B2 |
| APPLICATION NO. | : 16/521466 |
| DATED | : November 23, 2021 |
| INVENTOR(S) | : Pierric Deransart et al. |

Page 1 of 1

It is certified that error appears in the above-identified patent and that said Letters Patent is hereby corrected as shown below:

In the Specification

At Column 8, Line 54, please change "the u feature" to --the guide feature--.

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*